United States Patent [19]
Gomi et al.

[11] Patent Number: 5,180,810
[45] Date of Patent: Jan. 19, 1993

[54] PROTEIN H CAPABLE OF BINDING TO IGG

[75] Inventors: Hideyuki Gomi, Osaka; Tatsunobu Hozumi, Toyonaka; Shizuo Hattori, Kobe; Chiaki Tagawa, Takatsuki; Fumitaka Kishimoto, Kawanishi, all of Japan; Lars Björck, Södra Sandby, Sweden

[73] Assignees: Sumitomo Chemical Co., Limited, Osaka, Japan; HighTech Receptor AB, Malmo, Sweden

[21] Appl. No.: 376,641

[22] Filed: Jul. 7, 1989

[30] Foreign Application Priority Data

Nov. 21, 1988 [JP] Japan .................. 63-295527
Mar. 9, 1989 [JP] Japan .................... 1-58434

[51] Int. Cl.$^5$ ............................................ C07K 13/00
[52] U.S. Cl. ............................ 530/350; 435/69.1
[58] Field of Search .............. 530/350; 435/69.1; 514/12

[56] References Cited

U.S. PATENT DOCUMENTS 4,883,754 11/1989 Boyle et al. ................... 435/177

OTHER PUBLICATIONS

Boyle & Reis Biotechnology s:697–703 (1987).
Heath & Cleary Proc. Natl. Acad Sci. 86:4741–4745 Jun. 1989.
Chemical Abstracts, vol. 96, (May 1982) Grubb et al: "Isolation and some properties of an IgG Fc-binding protein from group A streptococci type 15", & Int. Arch. Allergy App. Immunol. 1982, 67(4), 369–76.
The Journal of Immunology, vol. 138, No. 3, Feb. (1987) pp. 922–926, The American Association of Immunologists; F. A. Nardella et al.: "T15 group a streptococcal Fc receptor binds to the same location on IgG as staphylococcal protein A and IgG rheumatoid factors" p. 923, column 1, lines 10–16.
Infection and Immunity, vol. 55, No. 5, May (1987) pp. 1233–1238, American Society for Microbiology.
D. G. Heath et al.: "Cloning and expression of the gene for an immunoglobulin G Fc receptor protein from a group A streptococcus" Proceedings of the National Academy of Science USA, vol. 86, Jun. 1989, pp. 4741–4745.
D. G. Heath et al.: "FC-receptor and M-protein genes of group A streptococci are products of gene duplication".
Biotechnology, vol. 5, Jul. 1987, pp. 697–703; M.D.P. Boyle et al.: "Bacterial Fc receptors" pp. 699–700.
The Journal of Immunology, vol. 133, No. 2, 969–974 (1984).
Journal of Bacteriology, vol. 167, No. 3, 870–880 (1986).
Cancer, vol. 46, 675–684 (1980).
TibTech, vol. 5, 79–83 (1987).
Gene, vol. 33, 103–119 (1985).
Proc. Natl. Acad. Sci. USA, vol. 74, No. 12, 5463–5467 (1977).
DNA, vol. 4, No. 2, 165–170 (1985).
Proc. Natl. Acad. Sci. USA, vol. 80, 1194–1198 (1983).
The Journal of Biological Chemistry, vol. 241, No. 13, 3055–3062 (1966).
Acta. Pathol. Microbiol. Scand., vol. 56, 295–304 (1962).
The Journal of Biological Chemistry, vol. 259, 1695–1702 1984.
Scand. J. Immunol., vol. 24, 549–557 (1986).
Int. Archs Allergy appl. Immun., vol. 67, 369–376 (1982).
Expl. Cell Biol., vol. 46, 146–151 (1978).

Primary Examiner—David L. Lacey
Assistant Examiner—Nina Ossanna

[57] ABSTRACT

A gene coding for Protein H, which is capable of binding specifically to human IgG of all subclasses, was isolated from Streptococcus sp. AP1 and expressed in host cells, E. coli to produce the Protein H.

6 Claims, 11 Drawing Sheets

Fig. 1 (A)

```
                                        10
MET THR ARG GLN GLN THR LYS LYS ASN TYR SER LEU ARG LYS LEU
                    20                                      30
LYS THR GLY THR ALA SER VAL ALA VAL ALA LEU THR VAL LEU GLY
                                        40
ALA GLY PHE ALA ASN GLN THR THR VAL LYS ALA GLU GLY ALA LYS
                    50                                      60
ILE ASP TRP GLN GLU GLU TYR LYS LYS LEU ASP GLU ASP ASN ALA
                                        70
LYS LEU VAL GLU VAL VAL GLU THR THR SER LEU GLU ASN GLU LYS
                    80                                      90
LEU LYS SER GLU ASN GLU GLU ASN LYS LYS ASN LEU ASP LYS LEU
                                        100
SER LYS GLU ASN GLN GLY LYS LEU GLU LYS LEU GLU LEU ASP TYR
                    110                                     120
LEU LYS LYS LEU ASP HIS GLU HIS LYS GLU HIS GLN LYS GLU GLN
                                        130
GLN GLU GLN GLU GLU ARG GLN LYS ASN GLN GLU GLN LEU GLU ARG
                    140                                     150
LYS TYR GLN ARG GLU VAL GLU LYS ARG TYR GLN GLU GLN LEU GLN
                                        160
LYS GLN GLN GLN LEU GLU THR GLU LYS GLN ILE SER GLU ALA SER
                    170                                     180
ARG LYS SER LEU SER ARG ASP LEU GLU ALA SER ARG ALA ALA LYS
                                        190
LYS ASP LEU GLU ALA GLU HIS GLN LYS LEU GLU ALA GLU HIS GLN
```

Fig. 1 (B)

```
                200                                          210
LYS LEU LYS GLU ASP LYS GLN ILE SER ASP ALA SER ARG GLN GLY

220
LEU SER ARG ASP LEU GLU ALA SER ARG ALA ALA LYS LYS GLU LEU 230                                          240
GLU ALA ASN HIS GLN LYS LEU GLU ALA GLU HIS GLN LYS LEU LYS

250
GLU ASP LYS GLN ILE SER ASP ALA SER ARG GLN GLY LEU SER ARG 260                                          270
ASP LEU GLU ALA SER ARG ALA ALA LYS LYS GLU LEU GLU ALA ASN

280
HIS GLN LYS LEU GLU ALA GLU ALA LYS ALA LEU LYS GLU GLN LEU 290                                      300
ALA LYS GLN ALA GLU GLU LEU ALA LYS LEU ARG ALA GLY LYS ALA

310
SER ASP SER GLN THR PRO ASP THR LYS PRO GLY ASN LYS ALA VAL 320                                  330
PRO GLY LYS GLY GLN ALA PRO GLN ALA GLY THR LYS PRO ASN GLN

340
ASN LYS ALA PRO MET LYS GLU THR LYS ARG GLN LEU PRO SER THR 350                                      360
GLY GLU THR ALA ASN PRO PHE PHE THR ALA ALA ALA LEU THR VAL

370
MET ALA THR ALA GLY VAL ALA ALA VAL VAL LYS ARG LYS GLU GLU

ASN
```

```
          10         20         30         40         50         60
 GAATTCCGTT ACCATCAACA GGTGAAACAG CTAACCCATT CTTCACAGCG GCAGCCCTTA 70         80         90        100        110        120
 CTGTTATGGC AACAGCTGGA GTAGCAGCAG TTGTAAAACG CAAAGAAGAA AACTAAGCTA 130        140        150        160        170        180
 TCACTTTGTA ATACTGAGTG AACATCAAGA GAGAACCAGT CGGTTCTCTC TTTTATGTAT 190        200        210        220        230        240
 AGAAGAATGA GGTTAAGGAG AGGTCACAAA CTAAACAACT CTTAAAAAGC TGACCTTTAC 250        260        270        280        290        300
 TCCTTTTGAT TAACTATATA TAATAAAAAT ATTAGGAAAA TAATAGCACT ATTAATTTTC 310        320        330        340        350        360
 TTTTTTAATA AAATCAAGGA GTAGATAATG ACTAGACAAC AAACCAAGAA AAATTATTCA 370        380        390        400        410        420
 CTACGGAAAC TAAAAACCGG TACGGCTTCA GTAGCCGTTG CTTTGACCGT TTTGGGCGCA 430        440        450        460        470        480
 GGTTTTGCAA ACCAAACAAC AGTTAAGGCG GAAGGGGCTA AAATTGATTG GCAAGAAGAG 490        500        510        520        530        540
 TATAAAAAGT TAGACGAAGA TAATGCTAAA CTTGTTGAGG TTGTTGAAAC CACAAGTTTG 550        560        570        580        590        600
 GAAAACGAAA AACTCAAGAG TGAGAATGAG GAGAATAAGA AAAATTTAGA CAAACTTAGC 610        620        630        640        650        660
 AAAGAAAATC AAGGAAAGCT CGAAAAATTG GAGCTTGACT ATCTCAAAAA ATTAGATCAC 670        680        690        700        710        720
 GAGCACAAAG AGCACCAAAA AGAACAACAA GAACAAGAAG AGCGACAAAA AAATCAAGAA 730        740        750        760        770        780
 CAATTAGAAC GTAAATACCA ACGAGAAGTA GAAAAACGTT ATCAAGAACA ACTCCAAAAA 790        800        810        820        830        840
 CAACAACAAT TAGAAACAGA AAAGCAAATC TCAGAAGCTA GTCGTAAGAG CCTAAGCCGT 850        860        870        880        890        900
 GACCTTGAAG CGTCTCGTGC AGCTAAAAAA GACCTTGAAG CTGAGCACCA AAAACTTGAA
```

Fig. 4 (B)

```
       910        920        930        940        950        960
  GCTGAGCACC AAAAACTTAA AGAAGACAAA CAAATCTCAG ACGCAAGTCG TCAAGGCCTA 970        980        990       1000       1010       1020
  AGCCGTGACC TTGAAGCGTC TCGTGCAGCT AAAAAGAGC TTGAAGCAAA TCACCAAAAA 1030       1040       1050       1060       1070       1080
  CTTGAAGCTG AGCACCAAAA ACTTAAAGAA GACAAACAAA TCTCAGACGC AAGTCGTCAA 1090       1100       1110       1120       1130       1140
  GGCCTAAGCC GTGACCTTGA AGCGTCTCGT GCAGCTAAAA AAGAGCTTGA AGCAAATCAC 1150       1160       1170       1180       1190       1200
  CAAAAACTTG AAGCAGAAGC AAAAGCACTC AAAGAACAAT TAGCGAAACA AGCTGAAGAA 1210       1220       1230       1240       1250       1260
  CTTGCAAAAC TAAGAGCTGG AAAAGCATCA GACTCACAAA CCCCTGATAC AAAACCAGGA 1270       1280       1290       1300       1310       1320
  AACAAAGCTG TTCCAGGTAA AGGTCAAGCA CCACAAGCAG GTACAAAACC TAACCAAAAC 1330       1340       1350       1360       1370       1380
  AAAGCACCAA TGAAGGAAAC TAAGAGACAG TTACCATCAA CAGGTGAAAC AGCTAACCCA 1390       1400       1410       1420       1430       1440
  TTCTTCACAG CGGCAGCCCT TACTGTTATG GCAACAGCTG GAGTAGCAGC AGTTGTAAAA 1450       1460       1470       1480       1490       1500
  CGCAAAGAAG AAAAACTAAGC TATCACTTTG TAATACTGAG TGAACATCAA GAGAGAACCA 1510       1520       1530       1540       1550       1560
  GTCGGTTCTC TCTTTTATGT ATAGAAGAAT GAGGTTAAGG AGAGGTCACA AACTAAACAA 1570       1580       1590       1600       1610       1620
  CTCTTAAAAA GCTGACCTTT ACTAATAATC GTCTTTGTTT TATAATGAAA ACATTAACGA 1630       1640       1650       1660       1670       1680
  AATAATTTAT TAAGGAGAGA ATACTAATGA ATATTAGAAA TAAGATTGAA AATAGTAAAA 1690       1700       1710       1720       1730       1740
  CACTACTATT TACATCCCTT GTAGCCGTGG CTCTACTAGG AGCTACACAA CCAGTTTCAG 1750       1760       1770       1780
  CCGAAACGTA TACATCACGC AATTTTGACT GGTCTGGGGA ATTC
```

Fig. 5 (A)

```
         10         20         30         40         50         60
ATGACTAGACAACAAACCAAGAAAAATTATTCACTACGGAAACTAAAAACCGGTACGGCT
MetThrArgGlnGlnThrLysLysAsnTyrSerLeuArgLysLeuLysThrGlyThrAla 70         80         90        100        110        120
TCAGTAGCCGTTGCTTTGACCGTTTTGGGCGCAGGTTTTGCAAACCAAACAACAGTTAAG
SerValAlaValAlaLeuThrValLeuGlyAlaGlyPheAlaAsnGlnThrThrValLys 130        140        150        160        170        180
GCGGAAGGGGCTAAAATTGATTGGCAAGAAGAGTATAAAAAGTTAGACGAAGATAATGCT
AlaGluGlyAlaLysIleAspTrpGlnGluGluTyrLysLysLeuAspGluAspAsnAla 190        200        210        220        230        240
AAACTTGTTGAGGTTGTTGAAACCACAAGTTTGGAAAACGAAAAACTCAAGAGTGAGAAT
LysLeuValGluValValGluThrThrSerLeuGluAsnGluLysLeuLysSerGluAsn 250        260        270        280        290        300
GAGGAGAATAAGAAAAATTTAGACAAACTTAGCAAAGAAAATCAAGGAAAGCTCGAAAAA
GluGluAsnLysLysAsnLeuAspLysLeuSerLysGluAsnGlnGlyLysLeuGluLys 310        320        330        340        350        360
TTGGAGCTTGACTATCTCAAAAAATTAGATCACGAGCACAAAGAGCACCAAAAAGAACAA
LeuGluLeuAspTyrLeuLysLysLeuAspHisGluHisLysGluHisGlnLysGluGln 370        380        390        400        410        420
CAAGAACAAGAAGAGCGACAAAAAAATCAAGAACAATTAGAACGTAAATACCAACGAGAA
GlnGluGlnGluGluArgGlnLysAsnGlnGluGlnLeuGluArgLysTyrGlnArgGlu 430        440        450        460        470        480
GTAGAAAAACGTTATCAAGAACAACTCCAAAAACAACAACAATTAGAAACAGAAAAGCAA
ValGluLysArgTyrGlnGluGlnLeuGlnLysGlnGlnGlnLeuGluThrGluLysGln 490        500        510        520        530        540
ATCTCAGAAGCTAGTCGTAAGAGCCTAAGCCGTGACCTTGAAGCGTCTCGTGCAGCTAAA
IleSerGluAlaSerArgLysSerLeuSerArgAspLeuGluAlaSerArgAlaAlaLys 550        560        570        580        590        600
AAAGACCTTGAAGCTGAGCACCAAAAACTTGAAGCTGAGCACCAAAAACTTAAAGAAGAC
LysAspLeuGluAlaGluHisGlnLysLeuGluAlaGluHisGlnLysLeuLysGluAsp
```

Fig. 5 (B)

```
         610        620        630        640        650        660
AAACAAATCTCAGACGCAAGTCGTCAAGGCCTAAGCCGTGACCTTGAAGCGTCTCGTGCA
LysGlnIleSerAspAlaSerArgGlnGlyLeuSerArgAspLeuGluAlaSerArgAla 670        680        690        700        710        720
GCTAAAAAAGAGCTTGAAGCAAATCACCAAAAACTTGAAGCTGAGCACCAAAAACTTAAA
AlaLysLysGluLeuGluAlaAsnHisGlnLysLeuGluAlaGluHisGlnLysLeuLys 730        740        750        760        770        780
GAAGACAAACAAATCTCAGACGCAAGTCGTCAAGGCCTAAGCCGTGACCTTGAAGCGTCT
GluAspLysGlnIleSerAspAlaSerArgGlnGlyLeuSerArgAspLeuGluAlaSer 790        800        810        820        830        840
CGTGCAGCTAAAAAAGAGCTTGAAGCAAATCACCAAAAACTTGAAGCAGAAGCAAAAGCA
ArgAlaAlaLysLysGluLeuGluAlaAsnHisGlnLysLeuGluAlaGluAlaLysAla 850        860        870        880        890        900
CTCAAAGAACAATTAGCGAAACAAGCTGAAGAACTTGCAAAACTAAGAGCTGGAAAAGCA
LeuLysGluGlnLeuAlaLysGlnAlaGluGluLeuAlaLysLeuArgAlaGlyLysAla

910        920        930        940        950        960
TCAGACTCACAAACCCCTGATACAAAACCAGGAAACAAAGCTGTTCCAGGTAAAGGTCAA
SerAspSerGlnThrProAspThrLysProGlyAsnLysAlaValProGlyLysGlyGln

970        980        990       1000       1010       1020
GCACCACAAGCAGGTACAAAACCTAACCAAAACAAAGCACCAATGAAGGAAACTAAGAGA
AlaProGlnAlaGlyThrLysProAsnGlnAsnLysAlaProMetLysGluThrLysArg 1030       1040       1050       1060       1070       1080
CAGTTACCATCAACAGGTGAAACAGCTAACCCATTCTTCACAGCGGCAGCCCTTACTGTT
GlnLeuProSerThrGlyGluThrAlaAsnProPhePheThrAlaAlaAlaLeuThrVal 1090       1100       1110       1120       1130
ATGGCAACAGCTGGAGTAGCAGCAGTTGTAAAACGCAAAGAAGAAAACTAA
MetAlaThrAlaGlyValAlaAlaValValLysArgLysGluGluAsn***
```

PROTEIN H CAPABLE OF BINDING TO IGG

BACKGROUND OF THE INVENTION

The present invention relates to a novel protein binding specifically to the Fc fragment of human immunoglobulin G(IgG), a gene coding for the said protein and to a process for producing the said protein.

DESCRIPTION OF RELATED ART

It has been known that certain microorganisms produce a series of proteins known as bacterial Fc receptors which have affinity to the Fc fragment of immunoglobulin (Boyle et al., Bio/Technology 5, 697(1987)).

Typical examples of such proteins are Protein A derived from *Staphylococcus aureus* and Protein G derived from Streptococcus G148.

These Protein characteristically bind to the Fc fragment of immunoglobulin and are used for assay, purification and preparation of antibodies as well as clinical diagnosis and biological research.

They can also be used for treatment of cancers and autoimmune diseases in which the proteins immobilized onto insoluble carriers are used to adsorb or remove undesirable immune complexes from blood(Cancer 46, 675(1980)).

These known proteins have some undesirable properties as agents for purification of human monoclonal antibodies produced from non-human animal cells or for removal of excessive IgG from blood for the purposes of blood purification.

Protein A binds to IgGs of various animal species including human beings as well as human IgA, IgM and so on. Protein G binds only to IgG, but it binds both to human IgG and to IgGs of other animal species (Fahnestock, Trends in Biotechnology 5, 79 (1987)). Thus, their binding specificities are not so narrow that they can be used for assay, purification and adsorption or removal of human IgG.

Under the circumstances, development of a protein capable of binding specifically to human IgG has been demanded.

It was suspected that a protein which binds to human IgG(IgG1, IgG2, IgG3 and IgG4) but not to IgGs of other animal species would be present in cells of group A Streptococcus strains (Björck, J. Immunol., 133, 969(1984)). However, no such protein has been isolated. Two types of IgG-Fc-binding proteins have been isolated from group A Streptococcus, one of which binds to human IgG(IgG1, IgG2 and IgG4), pig IgG and rabbit IgG; and the other binds specifically to human IgG3 (Boyle et al., Bio/Technology 5, 697(1987)).

It has been unknown whether or not such IgG-Fc-binding protein which binds specifically to human IgG (IgG1, IgG2, IgG3 and IgG4) but which does not bind to IgGs of most other animal species and to human IgA, IgD, IgE and IgM exists and whether or not a sufficient amount of such protein can stably be obtained.

The present inventors have extensively studied seeking for proteins which specifically binds to human IgG, and, as a result, found that Streptococcus sp. AP1 belonging to group A Streptococcus produces the protein with the above-mentioned properties. They have also obtained the gene coding for the said protein and provided a process for producing the said protein by the utilization of the gene through further extensive studies.

Thus, the present invention provides a novel protein capable of specifically binding to human IgG, and useful for assay and purification of human IgG, removal or adsorption of excessive IgG from blood and for diagnosis of autoimmune diseases. It also provides a gene coding for the said protein and a process for producing the said protein in industrial scales.

The protein provided by the present invention, which is hereinafter referred to as Protein H, is a protein capable of binding to the Fc fragment of immunoglobulin and produced by a strain of group A Streptococcus and has the following binding specificity:

i) It binds to human IgG(IgG1, IgG2, IgG3 and IgG4) and rabbit IgG;
ii) It does not bind to IgGs of mouse, rat, bovine, sheep and goat;
iii) It does not bind to human IgA, IgD, IgE and IgM;

or the following binding specificity:

i) It strongly binds to human IgG(IgG1, IgG2, IgG3 and IgG4), human IgGFc and rabbit IgG;
ii) It weakly binds to pig IgG;
iii) It does not bind to IgGs of mouse, rat, bovine, sheep, goat and horse;
iii) It does not bind to human IgGFab, IgA, IgD, IgE and IgM.

The strain, Streptococcus sp. AP1 which produces the Protein H has been deposited at the Fermentation Research Institute, Japan, under the deposit No. FERMP-10374, and also under the deposit No. FERM BP-2371 according to the BUDAPEST TREATY ON THE INTERNATIONAL RECOGNITION OF THE DEPOSIT OF MICROORGANISMS FOR THE PURPOSES OF PATENT PROCEDURE.

The protein H can be produced by the genetic engineering technology using the gene coding for the Protein H.

Figure 1A:
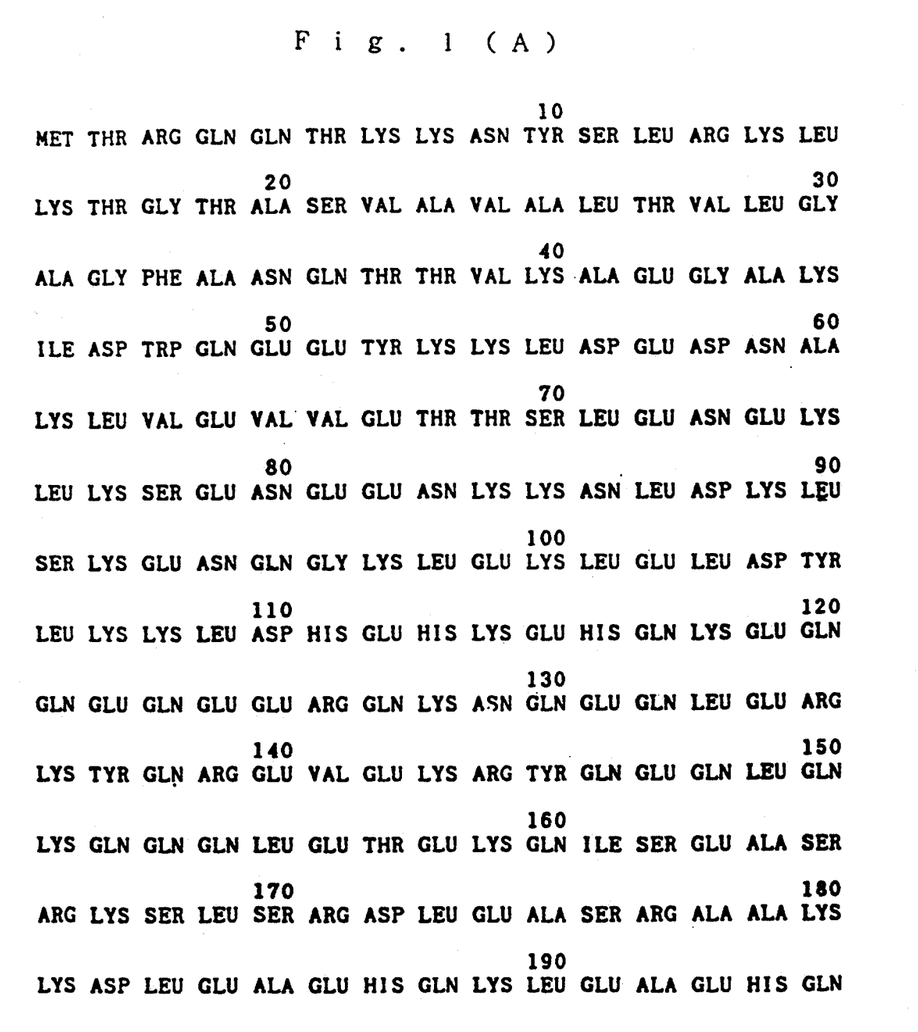
FIG. 1 represents the amino acid sequence of the Protein H.
Figure 1B:
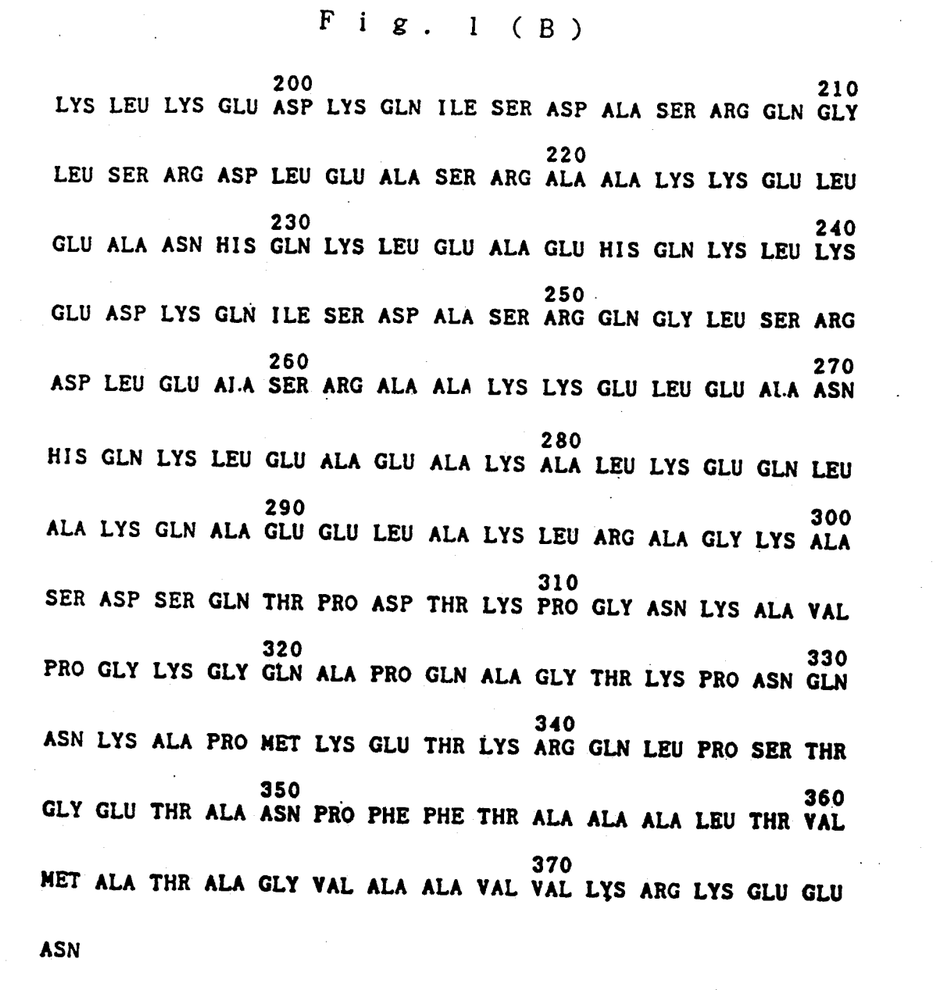

The Protein H produced from the gene isolated from the Streptococcus sp. AP1 has been found to be of the amino acid sequence given in the FIG. 1 by the analysis of the DNA sequences of the gene.

It is to be understood that subfragments or variants of the Protein H specifically disclosed in the present application wherein original amino acid sequence is modified or changed by insertion, addition, substitution, inversion or deletion of one or more amino acids are within the scope of the present invention as far as they retain the essential binding specificity as mentioned above.

The gene coding for the Protein H can be isolated from the chromosomal DNA of a Protein H-producing stain such as Streptococcus sp. AP1 based on the information on the DNA sequence of the Protein H shown in FIG. 4. The isolation of the gene can also be carried out as follows:

The chromosomal DNA can be isolated from cells of the Protein H-producing strain in accordance with a known method (Fahnestock, J. Bacteriol. 167, 870(1986)). The isolated chromosomal DNA is then segmented into fragments of adequate lengths by biochemical means such as digestion with a restriction enzyme or physical means.

The resulting fragments are then inserted at an adequate restriction site into an adequate cloning vector such as λgt11 (Young et al., Proc. Natl. Acad. Sci. USA 80, 1194 (1983)) or plasmid vectors such as pUC18 (Messing et al., Gene 33, 103 (1985)).

The vectors are then incorporated into adequate host cells such as *E. coli*.

From the resulting transformants, the clones producing the protein which binds to human IgG or the Fc region of human IgG are selected by a known method (Fahnestock et al., J. Bacteriol., 167, 870 (1986)).

Figure 2:
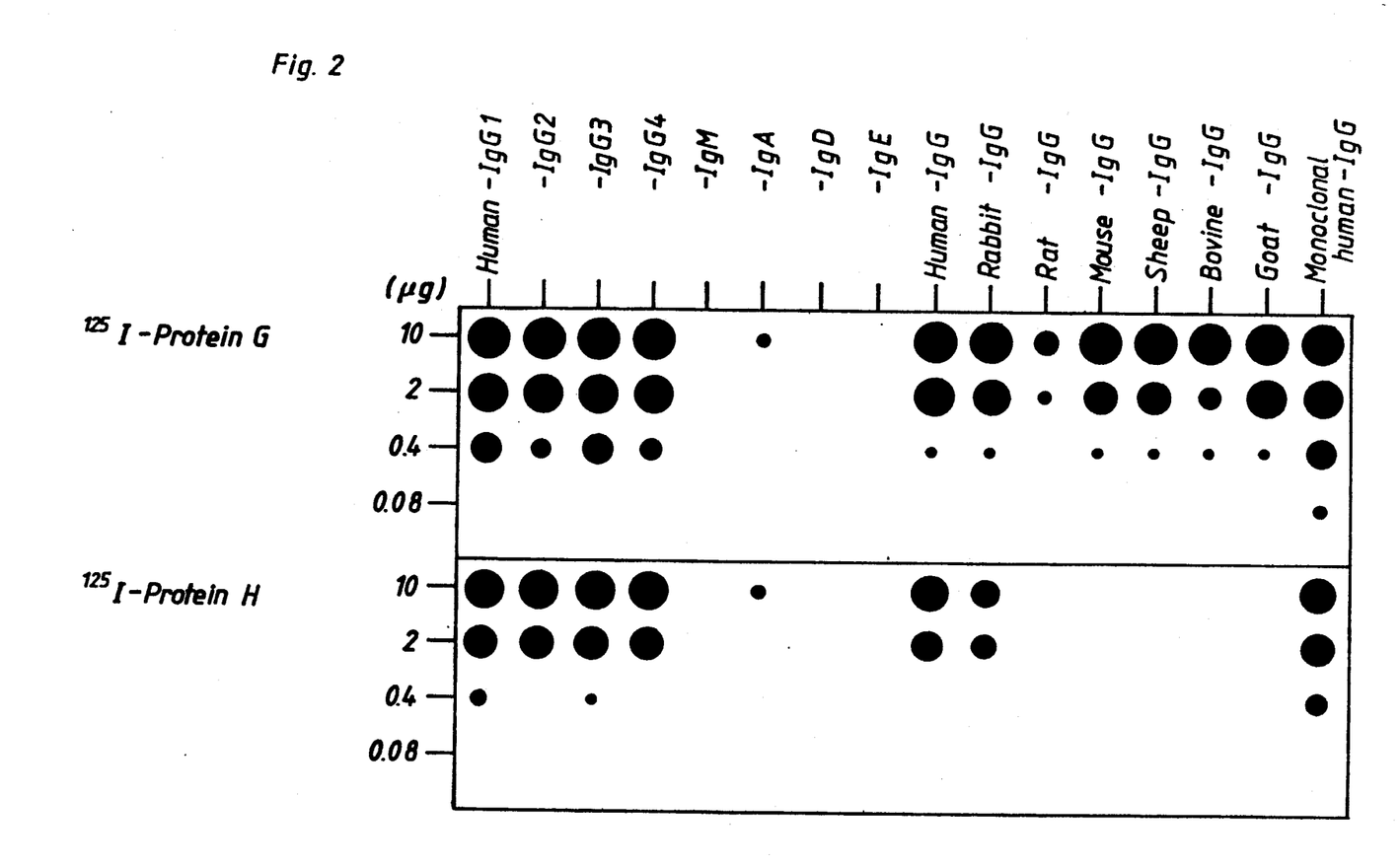
FIG. 2 gives autoradiograms showing binding specificities of Protein G and Protein H to various antibodies.

After the proteins capable of binding to human IgG or the Fc region of human IgG are isolated from the resulting positive clones according to a conventional method, the binding specificities of the proteins are determined to select the clones producing the Protein H. FIG. 2 shows the binding specificity of the Protein H.

Figure 4:
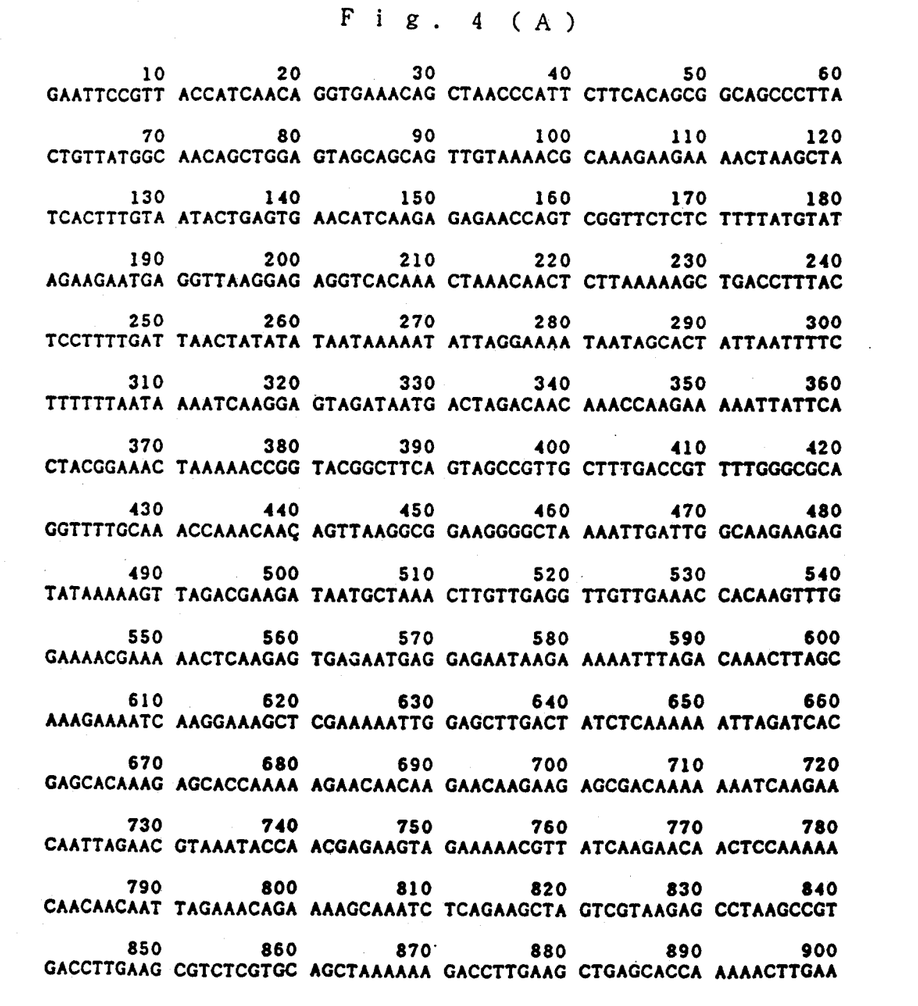
FIG. 4 gives the DNA sequence of the DNA insert in clone Fc4.
Figure 5:
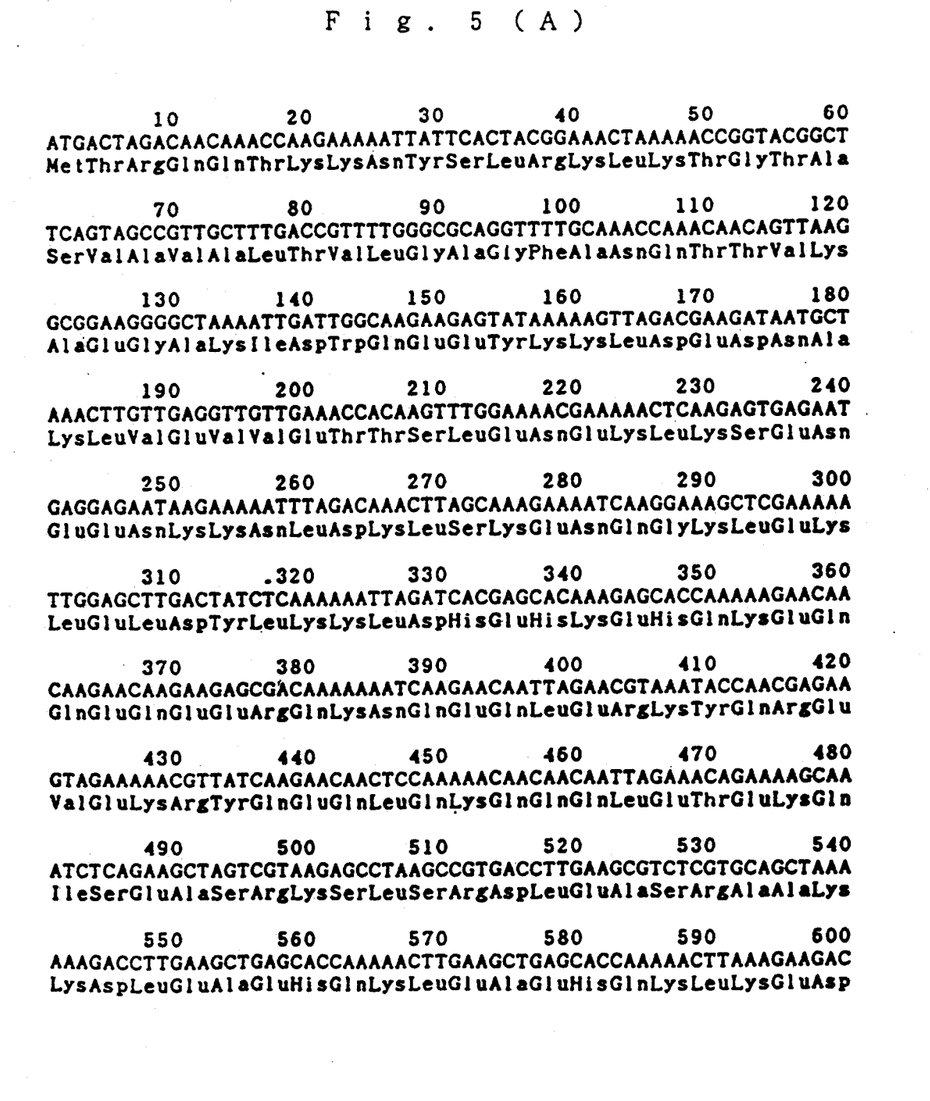
FIG. 5 gives the DNA sequence of the structural gene of the Protein H.

After the DNA insert of the said clone is isolated by a conventional method, the DNA sequence of the insert is determined by a known method (Sanger et al., Proc. Natl. Acad. Sci. USA 74, 5463 (1977); Choen et al., DNA 4, 165 (1985)). FIG. 4 shows the DNA sequence of the DNA insert isolated from the positive clone Fc4. FIG. 5 shows the DNA sequence of the structural gene coding for the Protein H isolated from the said clone.

It is necessary for genes to be expressed that they contain expression-controlling regions such as promoter, terminator and the like. The gene shown in FIG. 4 contains such as necessary expression-controlling regions.

The expression of genes may be effected with expression vectors having the necessary expression controlling regions in which only the structural gene is inserted. For this purpose, the structural gene shown in FIG. 5 can preferably be used. The structural gene coding for the Protein H can be obtained from the gene of FIG. 4 or synthesized by a conventional method based on the amino acid sequence given in the present specification.

As for the expression vectors, various host-vector systems have already been developed, from which the most suitable host-vector system can be selected for the expression of the gene of the present invention.

It has been known that, for each host cell, there is a particularly preferable codon usage for the expression of a given gene. In constructing a gene to be used for a given host-vector system, the codons preferable for the host should be used. Adequate sequences for the gene for the Protein H to be used in a particular host-vector system can be designed based on the amino acid sequence given in FIG. 1 and synthesized by a conventional synthetic method.

The present invention is further concerned with a process foraproducing the Protein H by culturing a host cell transformed with an expression vector in which the gene encoding the Protein H is inserted.

The process comprises steps of
i) inserting a gene coding for the Protein H into a vector;
ii) introducing the resulting vector into a suitable host cell;
iii) culturing the resulting transformant cell to produce the Protein H; and
iv) recovering the Protein H from the culture.

In the first step, the gene coding for the Protein H, which is isolated from the chromosmal DNA of Streptococcus sp. AP1 or synthesized as mentioned above, is inserted into a vector suitable for a host to be used for the expression of the Protein H. The insertion of the gene can be carried out by digesting the vector with a suitable restriction enzyme and linking thereto the gene by a conventional method.

In the second step, the resulting vector with the gene is introduced into host cells. The host cells may be Escherichia coli, Bacillus subtilis or Saccharomyces cerevisiae and the like. The introduction of the expression vector into the host cells can be effected in a conventional way.

In the third step, the resulting transformant cells are cultured in a suitable medium to produce the Protein H by the expression of the gene. The cultivation can be conducted in a conventional manner.

In the fourth step, the produced Protein H is recovered from the culture and purified, which can be conducted by a known method. For example, the cells are destroyed by a known method such as ultrasonification, enzyme treatment or grinding. The Protein H released out of the cells or secreted into the medium is recovered and purified by conventional methods usually used in the field of biochemistry such as ion-exchange chromatography, gel filtration, affinity chromatography using IgG as ligand, hydrophobic chromatography and reversed phase chromatography, which may be used solely or in suitable combinations.

As mentioned above, the protein provided by the present invention can be used for identification or separation of human IgG. For these purposes, the protein may be brought into a reagent kit or a pharmaceutical composition by mixing or combining it with suitable reagents, additives or carries.

The present invention will more precisely be described by the following examples. But, they are not intended to limit the scope of the present invention.

In the attached drawings.

EXAMPLE 1

IgG-binding activity of Streptococcus sp. AP1

To an Eppendorf tube was added 20 µl of dichloromethane solution of IODO-GEN TM (1,3,4,6-tetrachloro-3α, 6α-diphenyl glycouril; Pierce and Warriner Ltd.; 0.1 mg/ml), which was dried by blowing nitrogen gas in the tube, while the tube was inclined and rotated. To the resultant, 200 µl of a buffer solution A (50 mM Na-phosphate buffer pH 7.5, 0.01% Pluronic F-68 (BASF Corp.)) is added. After the mixture was allowed to stand in an ice bath for 10 minutes, the buffer was removed. To the tube were added 10 µl of 0.5M Na-phosphate buffer (pH 7.5) and 25 µl of IgG solution (human IgG 5 µg, mouse IgG 5 µg, human IgGFc 3.34 µg; Cappel Laboratories), followed by 2 µl of Na$^{125}$I solution (IMS 30, Carrier-free, 100 mCi/ml; Amersham Corp.). The mixture was allowed to stand for 15 minutes, while the mixture was ice-cooled and softly shaken. The reaction product was transferred to a serum tube containing 200 µl of a buffer solution (10 mM Na-phosphate buffer pH 7.2, 150 mM NaCl) after the serumtube had been treated with the buffer solution A (5 ml) in the same way as above-mentioned. The mixture was allowed to stand in an ice bath for 5 minutes. The resulting solution was applied to a PD-10 column (Pharmacia Fine Chemicals) equilibrated with buffer solution B (30 mM Na-phosphate buffer pH 7.3, 120 mM NaCl, 0.1% BSA) and eluted with buffer solution B. From each fraction (0.5 ml), 2 μl was sampled and measured with a γ-counter (Ria Gamma "QUATRO"; LKB Corp.) to recover the $^{125}$I-labeled IgG.

Thus, $^{125}$I-human IgG $2.24 \times 10^7$ cpm/μg ($1.12 \times 10^8$ cpm/ml), $^{125}$I-human IgGFc $8.98 \times 10^7$ cpm/μg ($3 \times 10^8$ cpm/ml) and $^{125}$I-mouse IgG $2.42 \times 10^7$ cpm/μg ($1.21 \times 10^8$ cpm/ml) were obtained.

A loopful of cells of Streptococcus sp. AP1 was inoculated to 5 ml of Todd-Hewitt culture medium (Difco Laboratories) and incubated at 37° C. for 10 hours. Of the culture solution, a 2 ml-portion was added to 100 ml of Todd-Hewitt medium, incubated at 37° C. for 13 hours, and centrifuged to harvest the cells.

The cells were washed with 100 ml of buffer solution C (30 mM Na-phosphate buffer pH 7.2, 120 mM NaCl, 0.05% Tween 20, 0.02% NaN$_3$) and diluted with buffer solution C to give suspensions of different cell concentrations between $10^7$ to $10^{10}$ cfu/ml. In a serum-tube were added a 200 μl-portion of each suspension, followed by $^{125}$I-labeled IgG (human IgG 10 ng human IgGFc 5.2 ng, mouse IgG 10 ng), and the mixture was stirred and allowed to stand at 37° C. still for 2 hours. After the reaction has completed, 2 ml of buffer solution C was added and centrifuged to harvest the cells. After similar retreatment of the cells with 2 ml of buffer solution C, the amount of $^{125}$I-labeled IgG bound to cells was measured with a γ-counter.

Figure 7:
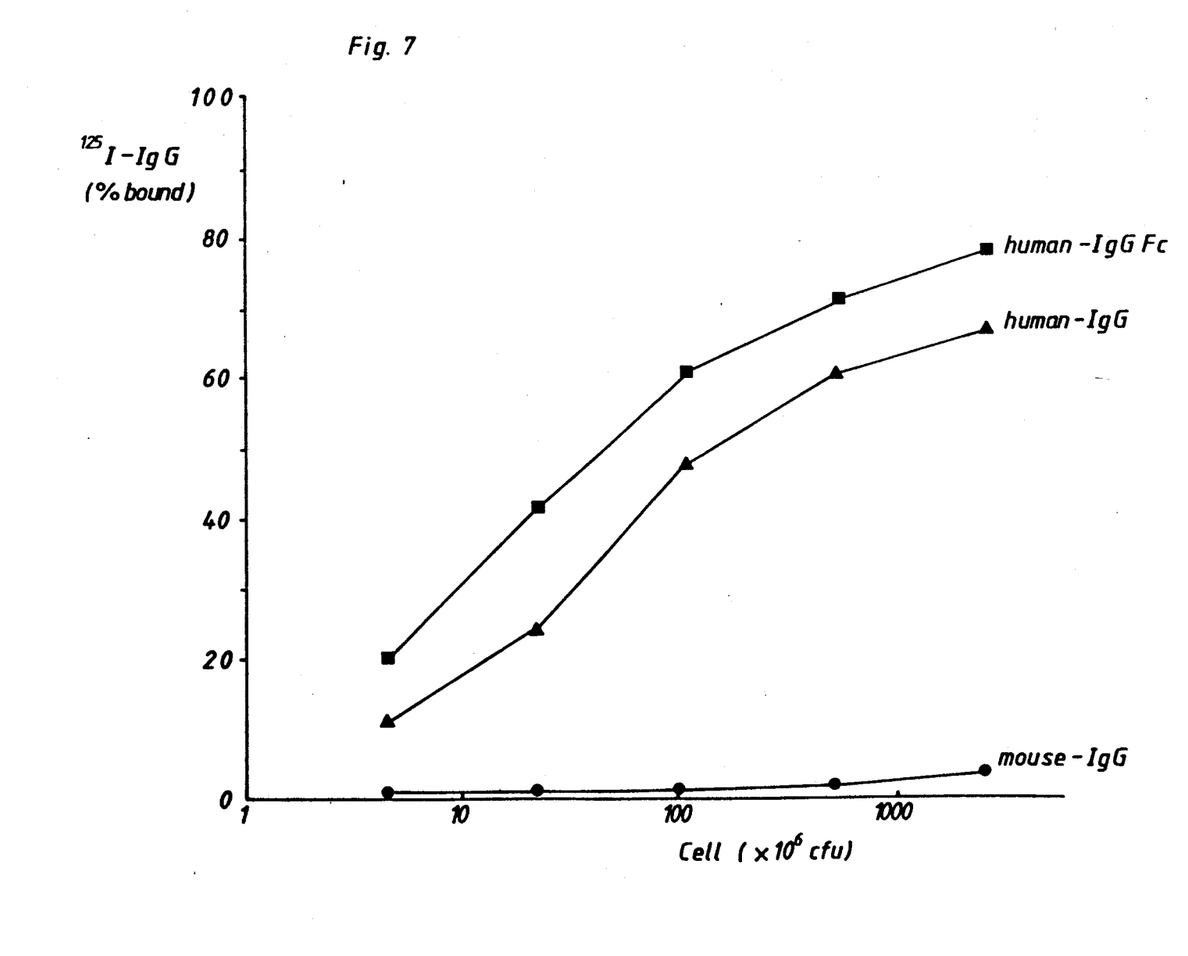
FIG. 7 is a graph showing the binding activity of Streptococcus sp. AP1 to human IgG, IgGFc and mouse IgG.

As the results in FIG. 7 show, Streptococcus sp. AP1 cell has proved to bind to human IgG and IgGFc but not to mouse IgG.

EXAMPLE 2

Preparation of chromosomal DNA of Streptococcus sp. AP1

A loopful of cells of Streptococcus sp. AP1 was inoculated to 10 ml of Todd-Hewitt culture medium and cultivated at 37° C. for 13 hours. Of the culture, a 8 ml-portion was added to 400 ml of Todd-Hewitt medium, and cultivated at 37° C. for 3 hours ($A_{660}=0.6$). After 22 ml of 10% cysteine and 26 ml of 0.4M DL-Threonine were added, the culture was again incubated for one hour. Then 250 ml of 15% glycine was added and cultivation was continued additionally for 2 hours. Cells were harvested by centrifugation and washed with 0.2M sodium acetate. The washed cells were suspended in 40 ml of buffer solution D (0.15M NaCl, 0.015M Na$_3$-citrate pH 7.4–7.6) containing 27% sucrose and 10 mM EDTA. To the suspension, 2500 units of Mutanolysin (Sigma Chemical Co.) was added and incubated at 37° C. for 3 hours. To the reaction mixture, 4 ml of 10% SDS and proteinase K (0.2 mg/ml) were added and incubated overnight at room temperature. After the extractions with phenol followed by ether, twice volume of cold ethanol were added to the removed water phase and the separated DNA was recovered by winding it around a glass rod.

The recovered DNA was dissolved in 5 ml of buffer solution D and incubated with RNase A (100 μg/ml) at 37° C. for 1 hour. Then phenol extraction and ethanol precipitation were carried out to recover DNA.

Yield of chromosomal DNA amounted to about 1 mg.

EXAMPLE 3

Cloning of Protein H gene

The chromosomal DNA (about 100 μg) obtained in Example 2 was dissolved in 200 μl of a buffer solution comprising 10 mM Tris.HCl (pH 7.5) and 1 mM EDTA and passed through a needle (27G) for use in injection to shear the DNA fragments of 2 to 10 kb. About 10 μg of the obtained DNA fragments was added to a solution comprising 40 mM Tris.HCl (pH 7.5), 5 mM DTT, 10 mM MgCl$_2$, 0.1 mg/ml BSA, 50 μM dNTP (dATP, dTTP, dGTP, dCTP) and 10 units of T4DNA polymerase and allowed to react at 24° C. for 2 hours to make them blunt-ended. Then phenol extraction and ethanol precipitation were carried out, and the thus-collected blunt ended DNA fragments were added to 50 μl of a solution comprising 100 mM Tris.HCl (pH 8.0), 100 mM NaCl, 1 mM EDTA, 80 μM S-adenosylmethionine and 200 units of EcoRI methylase and allowed to react at 37° C. for 20 minutes to make them methylated. Then phenol extraction and ethanol precipitation were carried out, and the thus-collected methylated DNA fragments were reacted at 16° C. for 12 hours with a commercially-available EcoRI linker which had already been phospholylated by the use of a commercially available ligation kit (Takara Shuzo Co., Ltd., Japan). The resulting reaction product was added to a solution comprising buffer E (10 mM Tris.HCl (pH 7.5), 100 mM NaCl, 10 mM MgCl$_2$, 1 mM DTT) and 200 units of EcoRI, and allowed to react at 37° C. for 12 hours.

After termination of this reaction, phenol extraction and isopropanol precipitation were carried out to collect the DNA.

The thus-obtained DNA (about 0.5 μg) was reacted at 16° C. for 16 hours with 1 μg of λgt11 DNA (Protoclone TM λgt11 system: Promega Biotech Corp.) in 13 μl of a solution comprising buffer F (66 mM Tris.HCl pH 7.6, 6.6 mM MgCl$_2$, 10 mM DTT, 0.1 mM ATP) and 400 units of T4 DNA ligase.

The ligated DNAs were packaged into phage using in vitro packaging kit (Gigapack Gold; Stratagene Corp.) and used as gene library of Streptococcus sp. AP1. The packaging efficiency, as measured with E. coli Y1090, was $3.2 \times 10^6$ pfu/μg λgt11 DNA.

E. coli Y1090 was cultivated in LBM medium {LB medium (Bacto tryptone 1%, Yeast extract 0.5%, NaCl 0.5%; pH 7.2), 10 mM MgSO$_4$, 0.2% maltose, 50 μg/ml Ampicillin} to grow up to $A_{660}=0.6$. From this culture, 0.2 ml was collected and centrifuged to harvest cells.

The cells were suspended in 0.2 ml of buffer solution G (10 mM Tris.HCl pH 7.4, 10 mM MgSO$_4$, 0.01% gelatin), mixed with 100 μl of buffer solution G and 7.6 μl of the gene library phage particles solution ($5 \times 10^4$ pfu), and incubated at 37° C. for 20 minutes. To this reaction mixture, 7 ml of soft agar solution (LBM medium, 0.4% soft agar, 47° C.) was added, stirred, and overlaid onto a LBM plate (diameter 150 mm). After 3 hours' incubation at 42° C., the plate was covered with nitrocellulose filter (BA 85, diameter 142 mm; Schleicher and Shuell AG) which had been immersed in 20 mM IPTG solution for 5 minutes and dried, and incubated at 37° C. for 16 hours.

After the cultivation has been completed, nitrocellulose filter was taken off. Then procedure was proceeded at room temperature with slow shaking as follows:

The nitrocellulose filter was treated in 50 ml of buffer solution H (10 mM Veronal buffer pH 7.4, 0.15M NaCl)

for 5 minutes, and incubated for 1 hour in 50 ml of buffer solution H containing 0.25% gelatin and 0.25% Tween 20. After 3 hour incubation with human IgGFc fragment (2 μg/ml) (CAPPEL Corp.) in 40 ml of buffer solution H containing 0.1% gelatin, the filter was washed three times with 40 ml each of buffer solution H containing 0.1% gelatin for 10 minutes. Again 1 hour incubation with goat anti-human IgGFc (Peroxidase conjugate, affinity purified; Jackson Immunoresearch Laboratories Corp.; diluted 1,000 fold with buffer solution H containing 0.1% gelatin) in 40 ml of buffer solution H containing 0.1% gelatin was carried out, and the filter was washed with 40 ml of buffer solution H containing 0.1% gelatin three times each for 10 minutes, followed by 40 ml of buffer solution K (20 mM Tris.HCl pH 7.5, 0.5M NaCl) once for 5 minutes. This filter was immersed in a color-developing solution (20 mg 4-chloro-1-naphthol/6.6 ml methanol, 20 μl $H_2O_2$/33.4 ml buffer solution K) for 30 minutes. Out of 70,000 plaques, 17 purple-plaques were collected and suspended in 500 μl of buffer solution G. To the suspension, 10 μl of chloroform was added and allowed to stand for 40 minutes, and then centrifuged (10,000 rpm, 1 minute). The same procedure with the resulting supernatant was repeated to give stable clones Fc4 and Fc16.

The IgGFc-binding proteins produced by clone Fc4 and Fc16 had the same apparent molecular weight of 45 kDa as judged by the Western-blotting method.

Phage solutions of Fc4 and Fc16 (400 μl, about $10^{10}$ pfu/ml) each was mixed with culture of *E. coli* Y1090 (400 μl), to which soft agar solution (8 ml) was added. The resulting mixture was laid over 8 sheets of LB plates. After incubation at 37° C. for 16 hours, 15 ml of buffer solution M (50 mM Tris.HCl pH 7.5, 100 mM NaCl, 8.1 mM $MgSO_4$, 0.01% gelatin) was added every plate and shaken at 4° C. for 3 hours.

After the buffer solutions were collected, the plates were washed with buffer solution (2 ml/plate), which was then combined with the collected buffer solution. To the combined buffer solution, 2 ml of chloroform was added and the mixture was stirred and centrifuged at 7,000 rpm for 15 minutes.

The supernatant was again centrifuged (17,000 rpm; 3 hours). The recovered precipitate was suspended in 0.5 ml of buffer solution M, to which CsCl was added to a concentration of 0.5 mg/ml. The suspension was then centrifuged (22,000 rpm; 2 hours, 4° C.) to recover phage particles. The phase particle suspension was dialyzed against a buffer solution comprising 50 mM Tris.HCl, pH 8.0, 10 mM NaCl, and 10 mM $MgCl_2$. To the dialyzed solution, EDTA (final concentration 20 mM), SDS (final concentration 0.5%) and proteinase K (final concentration 50 μg/ml) were added, and the mixture was incubated at 65° C. for 1 hour, and extracted with phenol followed by chloroform.

The aqueous phase was dialyzed against a buffer solution comprising 10 mM Tris.HCl, pH 8.0, and 1 mM EDTA, and precipitated with ethanol to give DNA.

Figure 3:
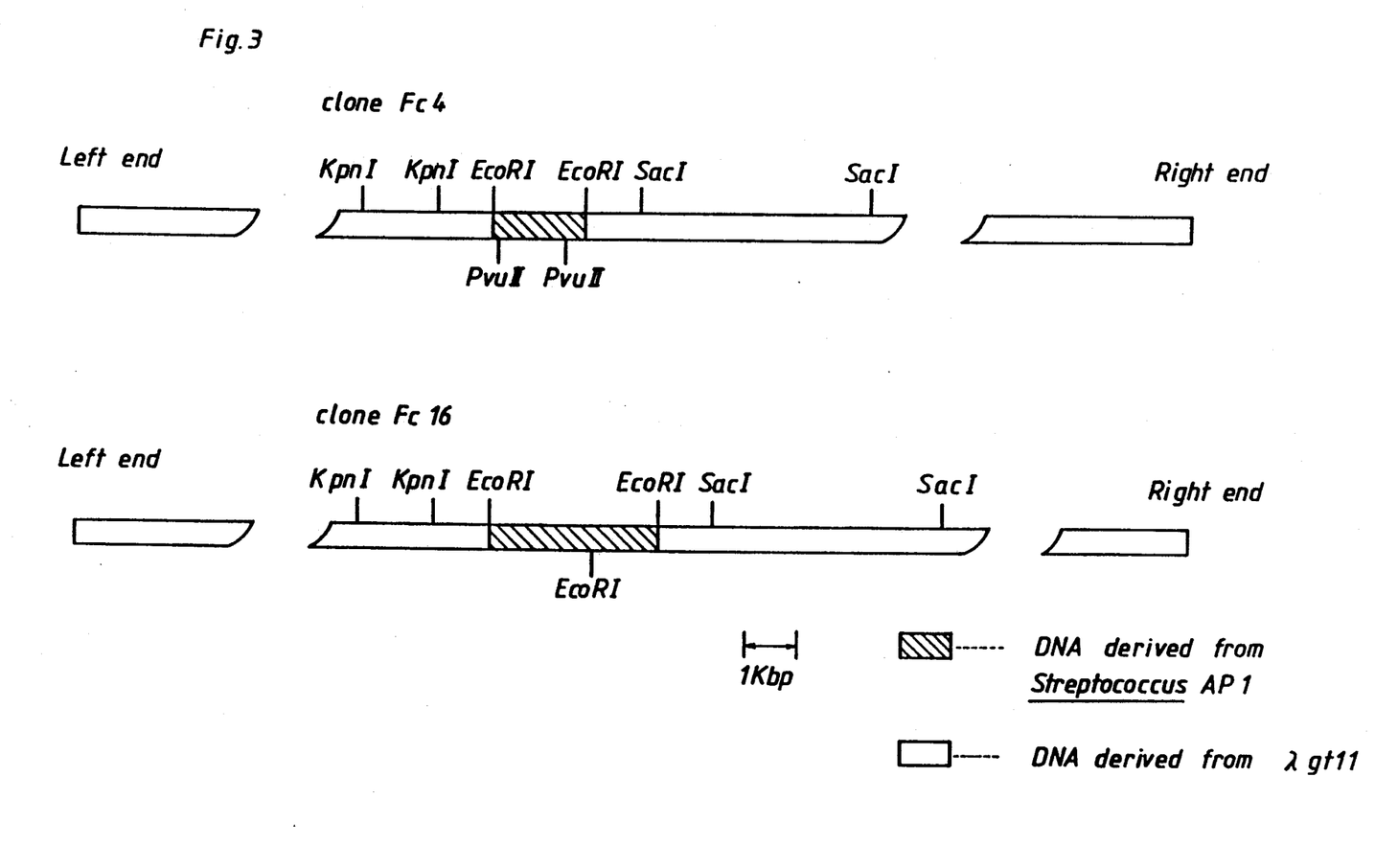
FIG. 3 is a diagram schematically illustrative of the DNA inserts of clones Fc4 and Fc16.

The obtained phage DNA (200 μg) was dissolved in 200 μl of a buffer solution comprising 10 mM Tris.HCl, pH 7.5, and 1 mM EDTA, and the restriction enzyme cleavage pattern was analyzed to find that clones Fc4 and Fc16 had respective DNA inserts as shown in FIG. 3.

*E. coli* Y1089 was lysogenized with phage clones Fc4 and Fc16 according to the methods described by Young et al. (Proc. Natl. Acad. Sci. USA 80, 1194 (1983)).

EXAMPLE 4

Binding specificity of Protein H

*E. coli* Y1089 lysogenized with phage Fc4 was inoculated to 40 ml of the aforesaid LBM medium and incubated at 28° C. for 16 hours. The seed culture was added to 2 liters of LBM medium and incubated at 28° C. for 145 minutes.

To the culture, IPTG was added to a final concentration of 1 mM and incubated at 42° C. for 45 minutes, and at 37° C. for additional 1 hour. The cells were harvested by centrifugation and suspended in 100 ml of a buffer solution comprising 50 mM phosphate buffer (pH 7.2), 5 mM EDTA, 5 mM benzamidine-HCl and 5 mM iodoacetamide and subjected to 10 minute ultrasonification. The mixture was centrifugated at a low speed to remove cell debris, and at 50,000 rpm for 30 minutes. The supernatant was applied to a IgG-Sepharose (6 Fast Flow; Pharmacia.) column (10 ml) which had been successively washed with 400 ml of buffer solution N (50 mM Tris.HCl pH 7.6, 150 mM NaCl, 0.05% Tween 20), 2.5M NaI (pH 7.2) and buffer solution N, and equilibrated with buffer solution N. After washing the column with 300 ml of buffer solution N, elution for recovering protein H was carried out with 40 ml of 2.5M NaI (pH 7.2).

Fractions of 0.5 ml each were collected and a small amount of sample collected from each fraction was spotted on a nitrocellulose filter. Then detection of Protein H containing fractions was carried out according to the staining method described in Example 3.

The Protein H-containing fractions were combined and dialyzed once against 1 liter of buffer solution comprising 50 mM phosphate buffer (pH 7.2), 0.15M NaCl and 0.25% NaI and twice against 5 liters each of buffer solution comprising 50 mM phosphate buffer (pH 7.2) and 0.15M NaCl, and then concentrated to about 1 ml with Amicon YM-5 (Amicon Corp.). The concentrated solution was applied to a gel filtration column for HPLC (diameter 7.5 mm × 6 cm, TSK gel G-3000 SW (Toyo Soda Co., Ltd.)) equilibrated with a buffer solution comprising 50 mM phosphate buffer (pH 7.5) and 0.2M NaCl, and eluted with the same buffer solution at a flow rate of 0.4 ml/min. The fractions collected between the 34th to 36th minute of elution, which contains Protein H, were combined and concentrated with Amicon YM-5. The concentrated solution was applied to a reversed phase HPLC column (diameter 4.6 mm × 7.5 cm, TSK gel Phenyl-5PW RP (Toyo Soda Co., Ltd.)) equilibrated with a buffer solution comprising 0.1M glycine/NaOH (pH 10.0) and 1 mM tetra-n-butyl ammonium hydroxide, and the Protein H was eluted with a linear gradient (0% →66%, 2% /min) of acetonitrile. Fractions collected near the 16th minute of elution, which contains Protein H, were combined and concentrated to about 2 ml under reduced pressure. The concentrated solution was applied to a PD-10 column (Pharmacia Corp.) equilibrated with water, and eluted with water to remove salts. Of the obtained protein, yield amounts to about 53 μg and molecular weight was about 45 kDa as measured by the Western-blotting technique using the staining method described in Example 3.

About 10 μg of Protein G (Genex Corp.) and about 10 μg of the aforesaid Protein H were labeled with $Na^{125}I$ according to the method described in Example 1 to give $1.28 \times 10^7$ cpm/μg ($8.5 \times 10^7$ cpm/ml) of $^{125}I$-

Protein G and 1.68×10⁷ cpm/μg (1.4×10⁸ cpm/ml) of ¹²⁵I-Protein H.

Human IgG1, IgG2, IgG3 and IgG4 (all, Protogen Corp.); human IgM, IgG and serum IgA, and IgGs of sheep, rabbit, bovine, and goat (all, Cappel Corp.); human IgD and IgE (all, Serotec Corp.); rat IgG (Jackson Immuno-research Corp.); mouse IgG (Zymed Corp.) and human monoclonal IgG were dissolved in buffer solution K, and diluted with buffer solution K to concentrations of 0.08 to 10 μg/200 μl. Each diluted solution (200 μl) was applied to nitrocellulose filter (Schleicher and Schuell Corp.) and adsorbed on the filter with BIO-DOT (BioRad Laboratories). The filter was incubated in 40 ml of a buffer solution comprising buffer K, 0.25% gelatin and 0.25% Tween-20 at 42° C. for 1.5 hours and washed twice in buffer solution K containing 0.1% gelatin at room temperature for 15 minutes. The washed filter was further incubated in 40 ml of a solution comprising buffer solution K, 0.1% gelatin and 0.5 μg (1.6×10⁵ cpm/ml) of ¹²⁵I-Protein G or 0.5 μg (2.1×10⁵ cpm/ml) of ¹²⁵I-Protein H at room temperature for 3 hours.

The filter was incubated 4 times with 40 ml of a solution comprising buffer solution K, 0.25% gelatin, 0.25% Tween-20 and 0.85 M NaCl at room temperature for 15 minutes for washing. After drying the filter, antibody-binding properties of Protein G and Protein H were analyzed by autoradiography.

The autoradiograms shown in FIG. 2 demonstrated that Protein H having the specificity of i) binding to human IgG (IgG1, IgG2, IgG3 and IgG4) and rabbit IgG, and ii) not binding to mouse, rat, bovine, sheep and goat IgG's and human IgA, IgD, IgE and IgM.

EXAMPLE 5

The nucleotide sequence of Protein H gene

The phage DNA (about 10 μg) of clone Fc4 obtained in Example 3 was incubated in 100 μl of a solution comprising buffer solution P (10 mM Tris.HCl, pH 7.5, 10 mM MgCl₂, 1 mM DTT), 30 units of Sac I and 42 units of KpnI at 37° C. for 5 hours. After termination of the reaction, phenol extraction and ethanol precipitation were carried out to recover phage DNA. On the other hand, plasmid pUC18 (about 8 μg) was incubated in 30 μl of a solution comprising buffer solution P, 20 units of SacI and 14 units of KpnI at 37° C. for 10 hours. Subsequently phenol extraction and ethanol precipitation were conducted to recover DNA. The recovered DNA was dissolved in 50 μl of 1 M Tris.HCl (pH 8.0) and incubated with 0.36 units of Bacterial Alkaline phosphatase (BAP) at 65° C. for 30 minutes. After 0.36 units of BAP was added, the reaction mixture was again incubated at 65° C. for further 30 minutes. Subsequently phenol extraction and ethanol precipitation were carried out to recover DNA.

Figure 6:
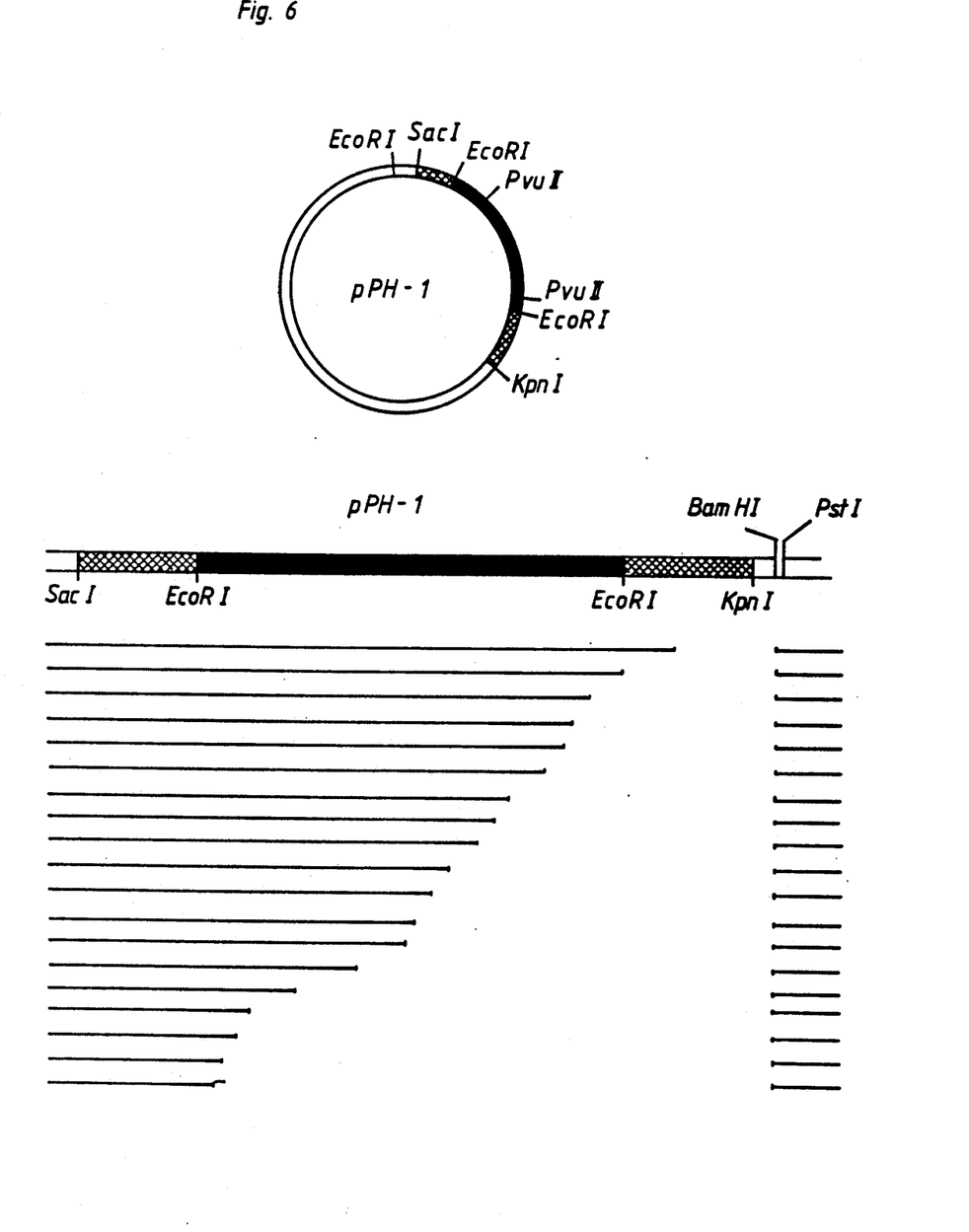
FIG. 6 illustrates a plasmid pPH-1 and its deletion plasmids used for determination of DNA sequence.

The BAP-treated pUC18 (0.5 μg) and the phage DNA digested with SacI and KpnI (0.1 μg) were incubated in 30 μl of a solution comprising buffer E and 10 units of T4 DNA ligase at 16° C. for 16 hours. With this reaction mixture, E. coli JM109 cells were transformed and ampicillin-resistant transformants were obtained, from which plasmid DNAs were prepared. By analysis of restriction enzyme cleavage pattern, a transformant containing a plasmid pPH-1 as shown in FIG. 6 was selected.

Plasmid pPH-1 (about 10 μg) was incubated in 25 μl of a solution comprising buffer E, 12 units of BamHI and 12 units of PstI at 37° C. for 8 hours. Then the resulting DNA was recovered by phenol extraction and ethanol precipitation, and treated with Deletion kit for Kilo-Sequence (Takara Shuzo Co., Ltd.). E. coli JM109 cells were transformed with the DNA and ampicillin-resistant transformants were obtained, from which plasmid DNAs were prepared. Subsequently by the analysis of the restriction enzyme cleavage pattern, transformants containing deletion plasmids shown in FIG. 6 were selected out.

The deletion plasmids and pPH-1 (about 3 μg each) were dissolved in 20 μl each of a solution comprising 2 μl of 2N NaOH and 2 μl of 2 mM EDTA and denaturated at room temperature for 5 minutes. The DNA was recovered by ethanol precipitation and the nucleotide sequence was determined with SEQUENASE (U.S. Biochemical), [α-³²P] dCTP (800 Ci/m mole; Amersham Co., Ltd.) and Primer M3 (Takara Shuzo Co., Ltd.).

The nucleotide sequence of the DNA fragment derived from the chromosomal DNA of Streptococcus sp. AP1 is as illustrated in FIG. 4. The DNA fragment contains promoter region, SD sequence, and the Protein H-structural gene coding for the amino acid sequence consisting of 376 amino acids (including Met at start point) starting from initiation codon ATG and terminating with termination codon TAA.

The structural gene encodes the amino acid sequence consisting of 376 residues beginning with Met and terminating with Asn, as shown in FIG. 5. The N-terminal amino acid sequence consisting of 41 residues beginning with Met and terminating with Ala has common characteristics to those of the signal sequence considered to be necessary for the protein secretion of gram positive bacteria, and therefore it can be considered that mature Protein H is a protein having an amino acid sequence consisting of 335 residues beginning with Glu and terminating with Asn.

EXAMPLE 6

Expression of pPH-1

The E. coli JM109 (pPH-1) obtained in Example 5, was cultivated in LB medium containing ampicillin at a concentration of 50 μg/ml at 37° C. for 16 hours. The culture was added to 2 liters of the same medium, incubated at 37° C. for 4.5 hours, and centrifuged.

The periplasmic fraction was prepared by the cold osmotic shock procedure (Nossal et al., J. Biol. Chem. 241, 3055 (1966). A mixture of the cytoplasmic and membrane fractions was prepared by sonicating the pellet obtained after cold osmotic shock.

In this procedure, more than 95% of the β-galactosidase activity was observed in the mixture of cytoplasmic and membrane fractions, while more than 95% of the β-lactamase activity was observed in the periplasmic fraction.

Both fractions were analysed by the Western-blotting method described in Example 3. The Protein H having an apparent molecular weight of 45 kDa was demonstrated only in the mixture of cytoplasmic and membrane fractions, while the Protein H having an apparent molecular weight of 42 kDa was demonstrated in the periplasmic fraction.

EXAMPLE 7

Binding properties of Protein H purified from the periplasmic fraction of *E. coli* JM109 (pPH-1)

The Protein H having an apparent molecular weight of 42 kDa was purified from the periplasmic fraction obtained in Example 6 by the successive chromatography of IgG-Sepharose and gel filtration according to the methods described in Example 4. Yield of the Protein H amounted to about 4 mg.

The N-terminal amino acid sequence of purified protein was determined by amino acid sequencer (Applied Biosystems model 477A amino acid sequencer; Applied Biosystems Corp.) to be Glu-Gly-Ala-Lys-Ile-Asp-Trp-Gln-Glu-Glu, which was inentical to the putative N-terminal amino acid sequence of nature Protein H as described in Example 5.

The purified Protein H was radiolabeled according to the methods described in Example 1. The binding properties of radiolabeled Protein H were determined according to the methods described in Example 4. In addition to immunoglobulins described in Example 4, binding to human IgGFc and human IgGFab (all, Cappel Corp.); and horse and pig IgG (all, Cooper Corp.) were also determined.

Figure 8:
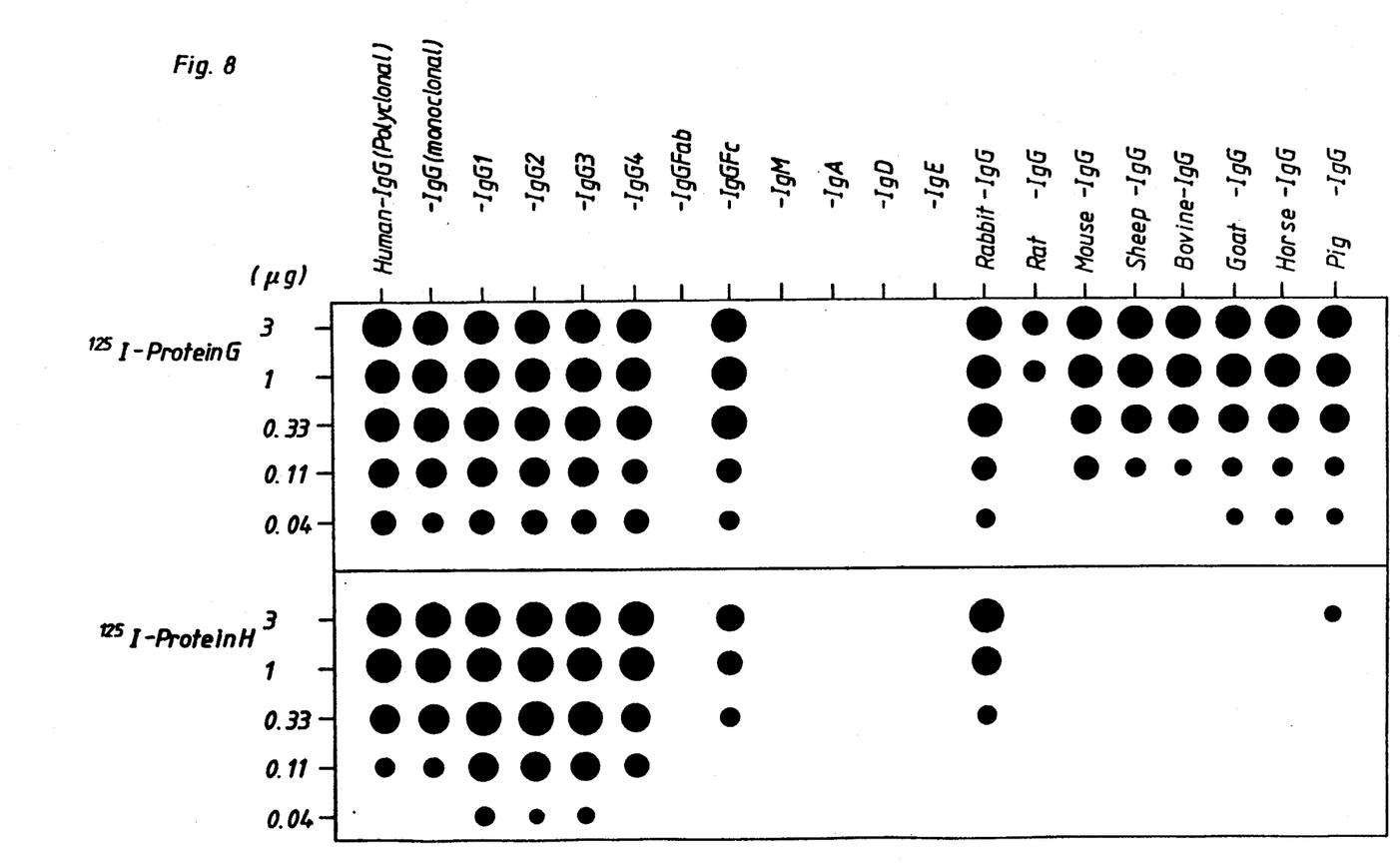
FIG. 8 gives autoradiograms showing binding specificities of Protein H purified from the periplasmic fraction of E. coli JM109 (pPH-1) and Protein G to various antibodies.

The autoradiograms shown in FIG. 8 demonstrated that Protein H having the specificity of
i) binding strongly to human IgG (IgG1, IgG2, IgG3 and IgG4), human IgGFc and rabbit IgG;
ii) binding weakly to pig IgG;
iii) not binding to IgGs of mouse, rat, bovine, sheep, goat and horse; and
iv) not binding to human IgGFab, IgA, IgD, IgE and IgM.

What is claimed is:

1. A purified protein produced by group A Streptococcus said protein being localized on the cell surface, having a molecular weight of 45 kilodaltons when measured by SDS-PAGE, and demonstrating specific binding to IgG1. IgG2, IgG3 and IgG4 of humans and to IgG of rabbits, or binding to the Fc portions thereof, and demonstrating a lack of affinity for the other classes of human immunoglobulin and bovine, mouse, rat, sheep, goat IgG.

2. A purified protein produced by group A Streptococcus said protein being localized on the cell surface, having a molecular weight of 42 kilodaltons when measured by SDS-PAGE, and demonstrating high affinity, specific binding to IgG1, IgG2, IgG3 and IgG4 of humans and to IgG of rabbits, or to the Fc portions thereof, demonstrating low affinity, specific binding to IgG or the Fc portion thereof, of pigs and demonstrating a lack of affinity for the Fab portion of human IgG, any part of the molecule of the other classes of human immunoglobulin and bovine, mouse, rat, sheep, goat or horse IgG.

3. The protein of claim 1, wherein said group A Streptococcus is Streptococcus sp. AP1.

4. A purified protein comprising a polypeptide of the amino acid sequence of FIG. 1 (A-B) from residues 42 (glutamic acid) in FIG. 1 (A) to 376 (asparagine) in FIG. 1 (B), inclusive, and demonstrating specific binding to IgG1, IgG2, IgG3 and IgG4 of humans and to IgG of rabbits, or such binding to the Fc portions thereof, and demonstrating a lack of affinity for the other classes of human immunoglobulin and bovine, mouse, rat, sheep, goat or horse IgG.

5. A pharmaceutical composition comprising the protein of claim 1, 2, 3 or 4 and a pharmaceutically acceptable additive or carrier.

6. A labelled polypeptide comprising the protein of claim 1, 2, 3 or 4 and a label.

* * * * *